United States Patent [19]

Kimble et al.

[11] Patent Number: 5,160,502
[45] Date of Patent: Nov. 3, 1992

[54] COMPOSITION OF MATTER AND METHOD OF OXIDATIVE CONVERSION OF ORGANIC COMPOUNDS THEREWITH

[75] Inventors: James B. Kimble, Bartlesville; John H. Kolts, Ochelata, both of Okla.

[73] Assignee: Phillips Petroleum Company, Bartlesville, Okla.

[21] Appl. No.: 945,123

[22] Filed: Dec. 22, 1986

[51] Int. Cl.$^5$ .................................................. C07C 2/00
[52] U.S. Cl. .................................... 585/500; 585/654; 585/656; 585/658; 585/660; 585/661; 585/945
[58] Field of Search .............. 585/500, 654, 656, 658, 585/660, 661, 943, 657

[56] References Cited

U.S. PATENT DOCUMENTS

| | | | |
|---|---|---|---|
| 3,784,483 | 1/1974 | Cichewski | 585/661 |
| 3,789,017 | 1/1974 | Walker | 585/661 |
| 3,793,225 | 2/1974 | Bertos | 585/661 |
| 3,793,392 | 2/1974 | Martin | 585/661 |
| 4,579,997 | 4/1986 | Kolts | 585/661 |
| 4,620,051 | 10/1986 | Kolts et al. | 585/661 |
| 4,620,052 | 10/1986 | Kolts et al. | 585/661 |
| 4,654,460 | 3/1987 | Kimble et al. | 585/661 |
| 4,658,081 | 4/1987 | Kolts | 585/661 |

FOREIGN PATENT DOCUMENTS 0177327  4/1986  European Pat. Off. ............ 585/700

Primary Examiner—Patrick P. Garvin
Assistant Examiner—E. D. Irzinski
Attorney, Agent, or Firm—K. K. Brandes

[57] ABSTRACT

A solid composition of matter comprising: (1) cobalt, (2) at least one metal selected from the group consisting of Group IA metals, (3) silicon and (4) oxygen, preferably containing at least two Group IA metals and optionally containing at least one material selected from the group consisting of halogen ions and compounds containing halogen ions, phosphorous and compounds containing phosphorous, sulfur and compounds containing sulfur. A method for the oxidative conversion of feed organic compounds to product organic compounds utilizing these solid compositions of matter as solid contact materials is described.

31 Claims, No Drawings

COMPOSITION OF MATTER AND METHOD OF OXIDATIVE CONVERSION OF ORGANIC COMPOUNDS THEREWITH

The present invention relates to an improved composition of matter. In a more specific aspect, the present invention relates to a solid contact material for the oxidative conversion of feed organic compounds to product organic compounds, in the presence of a free oxygen containing gas, and a method for such conversion.

BACKGROUND OF THE INVENTION

Numerous processes are in use and have been proposed for the conversion of organic compounds and feedstocks to more valuable organic compounds and more valuable feedstocks for use in the organic chemical and petrochemical industries, particularly organic compounds and feedstocks derived from petroleum sources.

One promising approach to such conversion has been the oxidative conversion of organic compounds to other organic compounds. However, in many cases, such oxidative conversion processes are not commercially viable, primarily because they are energy intensive, conversions of the feedstock are low, selectivity to the desired compounds is low and such processes cannot be utilized in a continuous manner. In most of such processes the feedstocks are contacted with a solid contact material. However, there is a difference of opinion among workers in the art concerning the nature of such processes, and, particularly, the function of the contact material and the manner in which such function is performed. For example, workers in the art have at one time or another suggested that the function of the contact material involves a purely physical phenomenon, an adsorption-desorption process, either of atomic or molecular oxygen, either on the surface or occluded within the solid material, oxidation-reduction, utilizing multivalent metals capable of oxidation-reduction, adsorption and desorption of the organic materials on the solid materials, a free radical mechanism, etc. Consequently, the solid materials utilized are referred to variously as "contact materials", "promoters", "activators" and "catalysts". Accordingly, in order to avoid functional categorization, the terms "solid contact material" or "solid contact materials" will be utilized in the present application.

Since many processes of the prior art are based on the theory that the contact materials function via adsorption-desorption of oxygen, oxidation-reduction, etc., such processes are operated in a cyclic manner by passing an oxidizing gas over the contact material, then contacting the feedstock with the oxygen containing contact material, and, thereafter, reactivating or regenerating the contact material by again passing a free oxygen containing gas thereover. Such processes thus require undesirably high temperatures, are energy intensive, since the exothermic and endothermic reactions occur separately, equipment costs are high, because of the necessity for rapid cycling, and the contact material's useful life is comparatively short.

From the above, it is quite clear that the suitability of contact materials for the oxidative conversion of organic compounds is unpredictable. It is, therefore, highly desirable that new and improved contact materials for such use be developed, and that improved processes utilizing such contact materials be provided, particularly processes which lower the temperatures necessary, lower the energy requirements, are capable of being carried out in a continuous manner, extend the useful life of the contact material, improve the conversion of the feedstock and improve the selectivity to the desired products.

Of the various feedstocks for the organic chemical and petrochemical industries, olefins, such as ethylene and propylene are of particular interest and have become major feedstocks. Of these, ethylene is by far the more important chemical feedstock since the demand for ethylene feedstocks is about double that for propylene feedstocks. Consequently, there is a definite need for materials and processes for the conversion of relatively inexpensive feedstocks to ethylene. At the present time, ethylene is produced almost exclusively by the dehydrogenation or pyrolysis of ethane and propane, naptha and, in some instances, gas oils. About 75% of the ethylene is produced at the present time by steam cracking of ethane and propane derived from natural gas, since natural gas contains from about 5 volume percent to about 60 volume percent of hydrocarbons other than methane, with the majority being ethane. However, relatively severe conditions, particularly temperatures in excess of about 1000° C., are required and, as indicated, such processes are highly energy intensive. In order to reduce the severity of the conditions, particularly temperature, numerous proposals to catalyze pyrolytic reactions have been made. While some of these processes do, in fact, reduce the severity of the conditions, the conversion of the feedstock and the selectivity to ethylene are still quite low. Of particular interest in this phase of the art, is the oxidative conversion of methane to higher hydrocarbons, particularly ethylene and ethane and, more particularly, ethylene. However, these processes have, heretofore resulted in low conversions of methane and poor selectivity to ethylene and ethane.

SUMMARY OF THE INVENTION

It is therefore an object of the present invention to provide an improved composition of matter and method of utilizing the same which overcomes the above and other disadvantages of the prior art. Another object of the present is to provide an improved composition of matter. Still another object of the present invention is to provide an improved contact material for the oxidative conversion of organic compounds to other organic compounds, in the presence of a free oxygen containing gas. Another and further object of the present invention is to provide an improved method for the oxidative conversion of organic compounds to other organic compounds, in the presence of a free oxygen containing gas. Another and further object of the present invention is to provide an improved method for the oxidative conversion of alkane hydrocarbons to other hydrocarbons, in the presence of a free oxygen containing gas. A further object of the present invention is to provide a method for the oxidative conversion of organic compounds to other organic compounds which results in improved conversion of feedstock. Yet another object of the present invention is to provide a method for the oxidative conversion of organic compounds to other organic compounds which results in improved selectivity to desired products. A further object of the present invention is to provide a method for the oxidative conversion of organic compounds to other organic compounds which results in improved conversion of feedstock and an improved selectivity to desired products. Another and further object of the present invention is to provide a method for the oxidative conversion of organic compounds to other organic compounds which utilizes temperatures below those of known processes. A still further object of the present invention is to provide a method for the oxidative conversion of organic compounds to other organic compounds which reduces the energy requirements thereof. Another object of the present invention is to provide a method for the oxidative conversion of organic compounds to other organic compounds which can be carried out in a continuous manner. Yet another object of the present invention is to provide a method for the oxidative conversion of organic compounds to other organic compounds which extends the useful life of the contact material utilized. These and other objects of the present invention will be apparent from the following detailed description.

A solid composition of matter, comprising: (1) cobalt, (2) at least one metal selected from the group consisting of Group IA metals, (3) silicon and (4) oxygen.

In a preferred embodiment, the composition contains at least two Group IA metals.

Optionally, the composition additionally contains at least one material selected from the group consisting of halogen ions and compounds containing halogen ions, phosphorous and compounds containing phosphorous and sulfur and compounds containing sulfur.

In another aspect, the present invention relates to a solid contact material, of the above compositions, adapted to convert feed organic compounds to product organic compounds in the presence of a free oxygen-containing gas.

The present invention further provides an improved method for the conversion of feed organic compounds to product organic compounds, comprising:

contacting said feed organic compounds and a free oxygen-containing gas with a solid contact material, comprising:

a solid contact material, comprising: (1) cobalt, (2) at least one metal selected from the group consisting of Group IA metals, (3) silicon and (4) oxygen, under oxidative conversion conditions sufficient to convert said feed organic compounds to product organic compounds.

DESCRIPTION OF THE PREFERRED EMBODIMENTS

The improved composition of matter of the present invention is generally a composition of matter, comprising (1) cobalt, (2) at least one metal selected from the group consisting of Group IA metals, (3) silicon and (4) oxygen, preferably containing at least two Group IA metals and optionally, containing at least one of a halogen, phosphorous and sulfur.

These improved compositions of matter are particularly useful as solid contact materials for the conversion of feed organic compounds to product organic compounds, such as the oxidative conversion of methane to higher hydrocarbons, and the oxidative dehydrogenation of $C_2$ to $C_7$ saturated hydrocarbons to less saturated hydrocarbons.

The preferred solid composition of matter is a composition of matter selected from the group consisting of:
(a) a solid composition of matter consisting essentially of: (1) cobalt, (2) at least one metal selected from the group consisting of Group IA metals, (3) silicon and (4) oxygen;

(b) a solid composition of matter consisting essentially of: (1) cobalt, (2) at least two metals selected from the group consisting of Group IA metals, (3) silicon and (4) oxygen;

(c) a solid composition of matter consisting essentially of: (1) cobalt, (2) at least one metal selected from the group consisting of Group IA metals, (3) silicon, (4) oxygen and (5) at least one material selected from the group consisting of halogen ions and compounds containing halogen ions, phosphorous and compounds containing phosphorous and sulfur and compounds containing sulfur; and (d) a solid composition of matter consisting essentially of: (1) cobalt, (2) at least two metals selected from the group consisting of Group IA metals, (3) silicon, (4) oxygen and (5) at least one material selected from the group consisting of halogen ions and compounds containing halogen ions, phosphorous and compounds containing phosphorous and sulfur and compounds containing sulfur.

The Group IA metals are preferably selected from the group consisting of lithium, sodium, potassium and rubidium. Preferably, the Group IA metals are lithium or sodium, and still more preferably, the combination of both lithium and sodium.

The preferred halogen is chlorine.

When utilized as a contact material for the oxidative conversion of feed organic compounds to product organic compounds, the cobalt, Group IA metals and silicon are in the form of oxides or oxide precursors which, upon drying and/or calcining, are converted to oxides. The halogen, when present, is preferably in the form of the halide, the phosphorous, when present, is preferably in the form of a phosphate or pyrophosphate and the sulfur, when present, is preferably in the form of a sulfide or sulfate.

When the term "effective amount" is utilized with reference to the composition of matter or contact materials herein, this term is meant to include more than an insignificant amount and, thus, a small amount sufficient to affect the function of the composition of matter for the purpose for which it is to be utilized.

Thus, the above compositions of matter or contact materials contain an effective amount of cobalt to near 100% of cobalt, for example, from 0.05 to 99.95 weight percent, expressed in terms of the metal based on the total weight of the catalyst composition. Preferably, however, due to the expense and difficulty of obtaining cobalt, it is preferred that cobalt be present in amounts of about 0.05 to 50 weight percent, preferably, 0.05 to 20 weight percent, still more preferably, between about 0.05 and 10 weight percent, again expressed in terms of elemental cobalt based on the total weight of the catalyst. The same principles apply to the content of the alkali metals, phosphorous, the halogen and the sulfur. However, the alkali metals, other than sodium, are preferably present in amounts between about 0.01 and 30 weight percent, and still more preferably, between about 0.5 and about 15 weight percent, expressed in terms of elemental alkali metal based on the total weight of the catalyst. Sodium may also be utilized in amounts between 0.01 and 30 weight percent but, as pointed out hereinafter, preferred amounts of sodium, when utilized in combination with another alkali metal, particularly, lithium, should be present in amounts between about 0.01 and 1.0 weight percent and between about 0.01 and 0.8 weight percent. The halogen, when present, is preferably present in amounts between 0.01 and 15 weight percent and, preferably, between about 0.01 and 5 weight percent. Preferred amounts of phosphorous and sulfur are also between about 0.01 and about 15 weight percent, preferably between about 0.01 and 5 weight percent, expressed in terms of the weight of the element based on the total weight of the catalyst. The balance of the composition of matter or contact material is, of course, silicon in the form of silica. Effective contact materials for the oxidative conversion reactions can be readily produced and, preferably, are produced by utilizing at least 50 percent by weight of silica and having the other components of the catalyst present in amounts less than about 50 weight percent.

The Group IA metal, cobalt, silicon, phosphorous, halide and sulfur can be derived from any suitable source of such materials, such as compounds in the form of carbonates, hydroxides, oxides, nitrates, octoates, halides, etc. The compositions of matter and contact materials can be prepared by any suitable method known in the art for the preparation of such materials in solid form. Particularly effective techniques are those utilized for the preparation of solid catalysts. Conventional methods include coprecipitation from an aqueous, an organic or a combination solution-dispersion, impregnation, dry mixing, wet mixing or the like, alone or in various combinations. In general, any method can be used which provides compositions of matter containing the prescribed components in effective amounts. Preferably, silica pellets can be impregnated with an aqueous solution of appropriate compounds and dried. In all cases, irrespective of how the components are combined, and irrespective of the source of the metal or elements, the dried composition is calcined in the presence of a free oxygen-containing gas, usually at temperatures between about 700° F. and about 1500° F. for from 1 to about 24 hours.

These compositions of matter and contact materials are particularly useful for the oxidative conversion of feed organic compounds to product organic compounds, in the presence of a free oxygen-containing gas. Processes of this character include the oxidative dehydrogenation of hydrocarbons, particularly alkanes having 2 to 7 carbon atoms, to other hydrocarbons, particularly ethylene, the oxidative methylation of toluene, in the presence of methane, to ethyl benzene and styrene, the oxidative conversion of toluene to stilbene, the oxidative methylation of acetonitrile, in the presence of methane, to acrylonitrile and $C_{2}+$ hydrocarbons and the oxidative methylation of other hydrocarbons. The compositions of matter and contact materials of the present invention are particularly useful for the oxidative conversion of methane to higher hydrocarbons, particularly the oxidative conversion of methane to ethylene, in the presence of a free oxygen-containing gas.

The conditions of operation of such processes for the oxidative conversion of feed organic compounds to product organic compounds can vary over a wide range. Such conditions are either known to those skilled in the art or can be readily optimized by one skilled in the art by simple, conventional experiments.

Since the composition of matter and contact materials of the present invention are highly effective for the oxidative conversion of methane to higher hydrocarbons, particularly, ethylene and ethane, and this process is of great value, the conversion of feed organic materials to product organic materials will be illustrated and exemplified by such methane conversion.

In accordance with most previous theories of the function and operation of contact materials for the oxidative conversion of methane to higher hydrocarbons, and, particularly, ethylene and ethane, the reaction has been carried out in the absence of a free oxygen-containing gas, with the oxygen theoretically being supplied by the contact material. As a result, the most utilized modes of operation have included treating the contact material with a free oxygen-containing gas, such as oxygen or air, for a period of time sufficient to produce a reducible oxide of a multivalent metal, thereafter, contacting methane with the reducible metal oxide and, thereafter, treating the metal oxide with a free oxygen-containing gas to "regenerate" the same. Similarly, certain contact materials are contacted with a free oxygen-containing gas to cause adsorption of oxygen on the contact material, methane is, thereafter, contacted with the contact material containing adsorbed oxygen and, thereafter, the contact material is again treated with a free oxygen-containing gas. In both instances, the contact material, after treatment with a free oxygen-containing gas, is usually purged with an inert gas, such as nitrogen, to remove excess oxygen which has not reacted with or been adsorbed on the contact material. Consequently, several techniques have been followed, including, carrying out the contact with methane and the contact with a free oxygen-containing gas in separate reaction chambers or sequentially passing a free oxygen-containing gas, a purge gas and methane through the contact material in a single reaction vessel. The disadvantages of either of these procedures will be evident to one skilled in the art.

In contrast to these prior art techniques, the method of the present invention is carried out by contacting methane with a contact material, in the presence of a free oxygen-containing gas.

In addition to methane, the hydrocarbon feedstock, employed in the method of the present invention, may contain other hydrocarbon or non-hydrocarbon components. The presence of ethane, propane and the like is not detrimental. It has been found that carbon dioxide and water are not detrimental, since they are most often products of the process. It has also been found that inert gases, such as nitrogen, helium and the like are not detrimental. Consequently, the method of the present invention can effectively utilize any conventional natural gas. To the extent that significant amounts of hydrogen sulfide are present in the natural gas, it is desirable to first remove the hydrogen sulfide, since it is believed that excessive amounts of this material can be detrimental to the method. Accordingly, a relatively inexpensive source of methane, namely, natural gas, can be employed without expensive separation or processing of the components thereof, with the exception of the relatively inexpensive removal of excess amounts of hydrogen sulfide. Other sources of methane or methane-containing gases can also be utilized.

The free oxygen-containing gas may be any suitable oxygen-containing gas, such as oxygen, oxygen-enriched air or air. The method of the present application has been effectively carried out utilizing air as a source of oxygen.

When utilized in the present invention, the term "diluent gas" is meant to include any gaseous material present in the methane-containing gas, the free oxygen-containing gas, or in the form of an added gas, which is essentially inert with respect to the oxidative conversion of methane and, thus, does not significantly decrease the conversion of methane and/or the selectivity to the product of higher hydrocarbons.

The volumetric ratio of methane to free oxygen should be in excess of about 1/1, preferably it is between about 1/1 and about 30/1 and still more preferably between about 4/1 and about 15/1. It has been found that a ratio of methane to free oxygen of at least about 1/1 is necessary, in accordance with the present invention, in order to obtain maximum conversion of methane and high selectivity to higher hydrocarbons, particularly ethylene.

In the present invention, it has been found that the method can be carried out between two extremes, namely, low conversion of methane/high selectivity to higher hydrocarbons, particularly ethylene, and high conversion of methane/low selectivity to the higher carbons, particularly ethylene. The process parameters (space velocity, temperature, and reactant partial pressure) can, to some extent, be used to control the reaction at the desired point between these two limits. Consequently, the reaction conditions may vary between broad limits.

The temperature is preferably at least about 500° C. and will generally vary between about 500° C. and about 1500° C. However, in order to obtain high conversions of methane and high selectivities to ethylene and ethane, the temperature is preferably between about 500° C. and about 900° C. and, most desirably, between about 600° C. and about 800° C.

It has also been found that, as the partial pressure of oxygen is increased, the selectivity to higher hydrocarbons decreases and the selectivity to carbon dioxide increases and vice versa. Total pressures may vary anywhere from around 1 atmosphere to about 1500 psi but are preferably below about 300 psi and ideally below about 100 psi.

Methane flow rates can also vary over a wide range, for example, from 0.5 to 100 cubic centimeters per minute per cubic centimeter of contact material. Preferably, however, the rate is between about 1.0 and about 75 cubic centimeters per minute per cubic centimeter of contact material.

The total flow velocities of all gaseous materials, including diluents, through a fixed bed reactor, may be at any rate effective for the oxidative conversion reaction. For example from 50 to 10,000 GHSV and preferably from 500 to 5000 GHSV.

In addition to the high conversion of methane and high selectivity to ethylene and ethane, attainable in accordance with the present invention, the contact materials are not readily poisoned and will tolerate the presence of water, carbon dioxide, carbon monoxide and the like. In addition, the contact materials appear to be long lived, with no noticeable deactivation problems. Concomitantly, the process can be carried out continuously in fixed, moving, fluidized, ebullating or entrained bed reactors.

Where the contact material is prepared without incorporation of a halide, such as chlorine, or the amount of halide present in the contact material is less than the desired effective amount, or the halogen content of the contact material becomes depleted during use, an effective amount of the halogen can be provided and maintained by preliminarily adding a halide or a halide precursor, for example, methyl chloride, to the reactor prior to conduct of the reaction and/or at least intervally adding a halide or a halide precursor during the course of the reaction.

The following examples illustrate the nature of the advantages of the present invention.

The contact materials of the examples were prepared by impregnating 10 grams of $Al_2O_3$ or $SiO_2$ with 5 grams of $Co(NO_3)_2.6H_2O$; 1 grams $NH_4Cl$; 0.1 gram $Na_4P_2O_7.10\ H_2O$ or 1.2 grams $LiNO_3$, as appropriate, and thereafter calcining the contact material as specified above. Contact materials were tested at a 1/1 $CH_4$/air ratio and a GHSV of 4,000.

Table I sets forth the results of a series of comparative tests. In Table I, the weight percent of a particular metal or element is set forth in terms of the weight percent of the element or metal based on the total weight of the contact material. The amount of chlorine was not known since a certain amount of the chlorine is lost during calculation and the contact materials were not analyzed for chlorine. In Run #2, the contact material was lithium deposited on quartz chips.

TABLE I

| Run No. | Wt. %-Metal | Temp (°C.) | Silica | | | | Alumina | | | |
|---|---|---|---|---|---|---|---|---|---|---|
| | | | Conv. (%) | Selectivity (%) | | | Conv. (%) | Selectivity % | | |
| | | | | $C_2=$ | $C_2$ | $C_2=/C_2$ | | $C_2=$ | $C_2$ | $C_2=/C_2$ |
| 1 | None | 700 | 4.7 | 0.0 | 4.9 | 0.00 | 11.6 | 0.0 | 1.1 | 0.00 |
|   |      | 800 | 6.1 | 4.0 | 10.4 | 0.38 | 13.9 | 0.0 | 0.7 | 0.00 |
| 2 | Li | 800 | 9.0 | 44.0 | 23.0 | 1.83 | — | — | — | — |
| 3 | 10-Co | 700 | 3.0 | 0.0 | 6.8 | 0.00 | 11.5 | 0.0 | 1.0 | 0.00 |
|   |       | 800 | 8.8 | 4.0 | 10.3 | 0.39 | 14.9 | 0.0 | 1.0 | 0.00 |
| 4 | 10-Co | 700 | 8.8 | 0.0 | 1.3 | 0.00 | 11.5 | 0.0 | 1.3 | 0.00 |
|   | Cl | 800 | 25.4 | 0.0 | 0.7 | 0.00 | — | — | — | — |
| 5 | 10-Co | 700 | 2.7 | 0.0 | 10.7 | 0.00 | 13.0 | 0.0 | 0.0 | 0.00 |
|   | 0.2-P | 800 | 8.4 | 7.9 | 14.7 | 0.54 | 13.4 | 0.9 | 0.9 | 0.00 |
|   | 0.35-Na | | | | | | | | | |
| 6 | 10-Co | 700 | 8.4 | 1.4 | 4.1 | 0.34 | 12.1 | 0.6 | 0.9 | 0.67 |
|   | Cl | 800 | 12.6 | 11.6 | 12.1 | 0.96 | 13.1 | 0.9 | 0.7 | 1.29 |
|   | 0.2-P | | | | | | | | | |
|   | 0.35-Na | | | | | | | | | |
| 7 | 10-Co | 700 | 1.6 | 3.3 | 28.1 | 0.12 | 12.1 | 0.9 | 2.1 | 0.43 |
|   | 3-Li | 800 | 10.6 | 24.9 | 29.0 | 0.86 | 14.0 | 5.2 | 5.2 | 1.0 |
|   | 0.35-Na | | | | | | | | | |
|   | 0.2-P | | | | | | | | | |
| 8 | 10-Co | 700 | 3.0 | 4.8 | 25.0 | 0.18 | 12.1 | 0.7 | 2.2 | 0.32 |
|   | 3-Li | 800 | 17.0 | 30.5 | 22.3 | 1.37 | 14.2 | 5.4 | 5.2 | 0.96 |
|   | 0.35-Na | | | | | | | | | |
|   | Cl | | | | | | | | | |
|   | 0.2-P | | | | | | | | | |

The following observations can be made concerning the results in Table I. Of the most common support materials, it is to be seen that silica is unique, whereas, alumina is not useful in the contact materials of the present invention. While cobalt on silica shows some improvement over silica alone, it is not a useful catalyst, to the extent that it is not selective to higher hydrocarbons, particularly, ethylene. It is also known from other parallel work that none of the other individual components, when deposited on silica, are useful catalysts. When small amounts of lithium are added to a cobalt and silica catalyst, a substantial improvement is seen and still further improvement is obtained when both lithium and sodium are present. Chlorine alone appears to be detrimental to the contact materials and phosphorous alone appears to have some effect but not a significant one. Both phosphorous and chlorine are effective when combined with sodium and/or lithium.

In a second series of tests, catalysts were prepared by impregnating silica with cobalt nitrate and lithium nitrate to produce a catalyst containing 10 weight percent cobalt and 3 weight percent lithium, respectively, expressed in terms of the element based on the total weight of the catalyst and with varying amounts of sodium nitrate. In Run No. 4 the sodium was in the form of $NaHPO_4$. As in the previous runs, the contact materials were tested at 1/1 $CH_4$/air ratio and a GHSV of 4,000.

Table II sets forth the results of this series of tests.

TABLE II

| Run No. | Wt. %-Na | Temp (°C.) | Conv. (%) | Selectivity (%) | | |
|---|---|---|---|---|---|---|
| | | | | $C_2=$ | $C_2$ | $C_2=/C_2$ |
| 1 | 0 | 700 | 4.7 | 1.1 | 8.4 | 0.13 |
| | | 800 | 12.9 | 13.6 | 16.6 | 0.82 |
| 2 | 0.1 | 700 | 4.3 | 2.3 | 10.8 | 0.21 |
| | | 800 | 13.2 | 19.3 | 20.7 | 0.93 |
| 3 | 0.2 | 700 | 2.1 | 4.1 | 30.8 | 0.13 |
| | | 800 | 13.5 | 29.6 | 28.0 | 1.06 |
| 4 | 0.2 | 700 | 2.6 | 3.5 | 22.3 | 0.16 |
| | | 800 | 12.6 | 27.0 | 29.1 | 0.93 |
| 5 | 0.4 | 700 | 1.1 | 7.3 | 53.6 | 0.14 |
| | | 800 | 9.7 | 33.9 | 35.8 | 0.95 |
| 6 | 0.8 | 700 | 5.1 | 0.0 | 9.1 | 0.00 |
| | | 800 | 11.2 | 4.6 | 25.8 | 1.18 |
| 7 | 1.6 | 700 | 3.7 | 0.0 | 10.7 | 0.00 |
| | | 800 | 9.4 | 1.2 | 20.8 | 0.06 |

It is to be observed from the previous Table that, when sodium is added to the cobalt and lithium containing contact material, the selectivity to higher hydrocarbons and, particularly, ethylene, deteriorates significantly when more than 0.8 weight percent of sodium is utilized.

Conditions for the oxidative dehydrogenation of $C_2$ to $C_7$ hydrocarbons can also vary over the same broad ranges useful for the oxidative conversion of methane to higher hydrocarbons and can be optimized by one skilled in the art by conventional, routine experimentation.

As a general rule, the conditions for the oxidative dehydrogenation of $C_2$ to $C_7$ hydrocarbons will fall within the lower part of the ranges previously specified for the oxidative conversion of methane to higher hydrocarbons. For example, a GSHV of 100 to 1000, and preferably 400 to 500, a hydrocarbon to oxygen ratio of 1/1 to 30/1, and preferably 1/1 to 3/1, a temperature of 600° to 775° C., and preferably 650° to 725° C., and a pressure of 0.5 to 10 atmospheres, and preferably 1 atmosphere, are highly effective.

While specific materials, conditions of operation, modes of operation and equipment have been referred to herein, it is to be recognized that these and other specific recitals are for illustrative purposes and to set forth the best mode only and are not to be considered limiting.

That which is claimed is:

1. A method for the oxidative conversion of methane to higher hydrocarbons comprising:
   contacting a feed material comprising methane and a free oxygen-containing gas with
   a solid contact material, comprising: (1) cobalt, (2) at least one metal selected from the group consisting of Group IA metals, (3) silicon and (4) oxygen,
   under conditions sufficient to convert said methane to said higher hydrocarbons.

2. A method in accordance with claim 1 wherein the cobalt, the Group IA metals and silicon are all in their oxide form.

3. A method in accordance with claim 1 wherein the Group IA metals are selected from the group consisting of sodium, lithium, and mixtures thereof.

4. A method in accordance with claim 3 wherein the Group IA metal is sodium.

5. A method in accordance with claim 3 wherein the Group IA metal is lithium.

6. A method in accordance with claim 3 wherein the Group IA metals are sodium and lithium.

7. A method in accordance with claim 1 wherein a material selected from the group consisting of halogens and halogen precursors is added at least intervally during the reaction.

8. A method in accordance with claim 1 wherein the contact material additionally comprises at least one material selected from the group consisting of phosphorous and compounds containing phosphorous, halogen ions and compounds containing halogen ions, sulfur and compounds containing sulfur.

9. A method in accordance with claim 8 wherein the contact material additionally comprises halogen ions or compounds containing halogen ions.

10. A method in accordance with claim 9 wherein the contact material initially contains insufficient amounts of halogen ions and the contact material is contacted with a material selected from the group consisting of halogens and halogen precursors prior to initiation of the process.

11. A method in accordance with claim 9 wherein the contact material initially contains insufficient amounts of halogen ions or compounds containing halogen ions and wherein at least one material selected from the group consisting of halogens and halogen precursors is at least intervally added to the reactor during the course of the reaction.

12. A method in accordance with claim 8 wherein the contact material additionally comprises sulfur or compounds containing sulfur.

13. A method in accordance with claim 12 wherein the contact material additionally comprises halogen ions or compounds containing halogen ions and phosphorous or compounds containing phosphorous.

14. A method in accordance with claim 1 wherein said solid contact material consists essentially of: (1) cobalt, (2) at least one metal selected from the group consisting of Group IA metals, (3) silicon and (4) oxygen.

15. A method of the oxidative dehydrogenation of feed organic compounds, comprising at least one saturated $C_2$ to $C_7$ hydrocarbon, to product organic compounds, comprising unsaturated hydrocarbons, comprising:

contacting said feed organic compounds and a free oxygen-containing gas with a solid contact material, consisting essentially of (1) cobalt, (2) at least one metal selected from the group consisting of Group IA metals, (3) silicon and (4) oxygen, under conditions sufficient to convert said feed organic compounds to said product organic compounds.

16. A method in accordance with claim 15 wherein the cobalt, the Group IA metals and silicon are all in their oxide form.

17. A method in accordance with claim 15 wherein the Group IA metals are selected from the group consisting of sodium, lithium and mixtures thereof.

18. A method in accordance with claim 17 wherein the Group IA metal is sodium.

19. A method in accordance with claim 17 wherein the Group IA metal is lithium.

20. A method in accordance with claim 17 wherein the Group IA metals are sodium and lithium.

21. A method in accordance with claim 15 wherein a material selected from the group consisting of halogens and halogen precursors is added to the reactor at least intervally during the reaction.

22. A method in accordance with claim 15 wherein said contact material further consists essentially of at least one material selected from the group consisting of phosphorus and compounds containing phosphorus, halogen ions and compounds containing halogen ions, sulfur and compounds containing sulfur.

23. A method in accordance with claim 22 wherein said contact material further consists essentially of halogen ions or compounds containing halogen ions.

24. A method in accordance with claim 23 wherein said contact material initially contains insufficient amounts of halogen ions and the contact material is contacted with a material selected from the group consisting of halogens and halogen precursors prior to initiation of the process.

25. A method in accordance with claim 23 wherein said contact material initially contains insufficient amounts of halogen ions or compounds containing halogen ions and wherein at least one material selected from the group consisting of halogens and halogen precursors is at least intervally added during the course of the reaction.

26. A method in accordance with claim 22 wherein said contact material further consists essentially of sulfur or compounds containing sulfur.

27. A method in accordance with claim 22 wherein said contact material further consists essentially of halogen ions or compounds containing halogen ions and phosphorus or compounds containing phosphorus.

* * * * *